(12) United States Patent
Engman et al.

(10) Patent No.: US 11,712,573 B2
(45) Date of Patent: Aug. 1, 2023

(54) MANAGING ALERTS IN A WCD SYSTEM

(71) Applicant: West Affum Holdings Corp., Grand Cayman (KY)

(72) Inventors: Zoie R. Engman, Kirkland, WA (US); Amanda K. Hall, Seattle, WA (US); Laura M. Gustavson, Redmond, WA (US); Aaron J. Piazza, Lake Forest Park, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 0 days.

(21) Appl. No.: 17/380,935

(22) Filed: Jul. 20, 2021

(65) Prior Publication Data
US 2022/0184407 A1 Jun. 16, 2022

Related U.S. Application Data

(60) Provisional application No. 63/126,453, filed on Dec. 16, 2020.

(51) Int. Cl.
*A61N 1/39* (2006.01)
(52) U.S. Cl.
CPC ......... *A61N 1/3904* (2017.08); *A61N 1/3925* (2013.01); *A61N 1/3968* (2013.01); *A61N 1/3993* (2013.01)
(58) Field of Classification Search
CPC ........ A61N 1/39–39046; A61N 1/3925; A61N 1/3993
See application file for complete search history.

(56) References Cited

U.S. PATENT DOCUMENTS

| | | |
|---|---|---|
| 3,724,455 A | 4/1973 | Unger |
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bomn et al. |
| 5,353,793 A | 10/1994 | Bomn |
| RE34,800 E | 11/1994 | Hutchins |
| 5,394,892 A | 3/1995 | Kenny |
| 5,405,362 A | 4/1995 | Kramer et al. |

(Continued)

FOREIGN PATENT DOCUMENTS

WO 1998039061 A2 9/1998

OTHER PUBLICATIONS

Pagan-Carlo, et al., "Encircling Overlapping Multipulse Shock Waveforms for Transthoracic Defibrillation," JACC Journals, Dec. 1998, vol. 32 Issue 7, p. 2065-2071.

(Continued)

*Primary Examiner* — Eric D. Bertram
(74) *Attorney, Agent, or Firm* — Columbia IP Law (57) ABSTRACT

In one embodiment, a method to alert a user of a wearable cardioverter defibrillator (WCD) is described. The method includes detecting a condition requiring attention of the patient and issuing an alert to notify the patient of the condition. The method also includes receiving a first input from the patient to replay the audible portion of the alert and replaying the audible portion of the alert when the first input is received.

20 Claims, 6 Drawing Sheets

(56) References Cited

U.S. PATENT DOCUMENTS

| | | | |
|---|---|---|---|
| 5,474,574 A | 12/1995 | Payne et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 * | 12/2001 | Nova | A61N 1/39044 607/5 |
| 6,356,785 B1 * | 3/2002 | Snyder | A61N 1/39044 607/5 |
| 6,427,083 B1 | 7/2002 | Owen et al. | |
| 6,437,083 B1 | 7/2002 | Owen et al. | |
| 6,529,875 B1 | 3/2003 | Nakajima | |
| 6,546,285 B1 | 4/2003 | Owen et al. | |
| 6,671,545 B2 | 12/2003 | Fincke | |
| 6,681,003 B2 | 1/2004 | Linder et al. | |
| 6,697,671 B1 * | 2/2004 | Nova | A61N 1/39044 607/5 |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,454,219 B2 | 9/2016 | Volpe et al. | |
| 9,592,403 B2 | 3/2017 | Sullivan | |
| 2003/0158593 A1 | 8/2003 | Heilman et al. | |
| 2004/0143298 A1 * | 7/2004 | Nova | A61N 1/3993 607/5 |
| 2005/0107833 A1 | 5/2005 | Freeman et al. | |
| 2005/0107834 A1 | 5/2005 | Freeman et al. | |
| 2005/0261742 A1 * | 11/2005 | Nova | A61N 1/3993 607/5 |
| 2006/0058848 A1 * | 3/2006 | Piraino | A61N 1/39044 607/5 |
| 2008/0312709 A1 | 12/2008 | Volpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 * | 5/2012 | Kaib | A61B 5/02438 340/539.12 |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0025131 A1 | 1/2014 | Sullivan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 * | 2/2015 | Kaib | A61N 1/3993 607/63 |
| 2015/0328472 A1 | 11/2015 | Sullivan et al. | |
| 2016/0004831 A1 | 1/2016 | Carlson et al. | |
| 2016/0082277 A1 | 3/2016 | Foshee, Jr. et al. | |
| 2018/0040255 A1 * | 2/2018 | Freeman | A61B 5/021 |

OTHER PUBLICATIONS

The LifeVest Network/Patient Data Management System, Zoll, 2015, 2000503 Rev A.

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

* cited by examiner

MANAGING ALERTS IN A WCD SYSTEM

CROSS REFERENCE TO RELATED PATENT APPLICATIONS

This patent application claims benefit of U.S. Provisional Patent Application No. 63/126,453 filed Dec. 16, 2020 and is incorporated herein by reference in their entirety for all purposes.

BACKGROUND

When people suffer from some types of heart arrhythmias, in some instances, blood flow to various parts of the body may be reduced. Some arrhythmias can result in a Sudden Cardiac Arrest (SCA). SCA can lead to death very quickly, e.g., within 10 minutes, unless treated in the interim. Some observers have thought that SCA is the same as a heart attack, which it is not.

Some people have an increased risk of SCA. Such people may include patients who have had a heart attack or a prior SCA episode. A frequent recommendation for these people is to receive an Implantable Cardioverter Defibrillator (ICD). The ICD is surgically implanted in the chest, and continuously monitors the patient's intracardiac electrogram (IEGM). If certain types of heart arrhythmias are detected, then the ICD delivers an electric shock through the heart.

As a further precaution, people who have been identified to have an increased risk of a SCA are sometimes given a Wearable Cardioverter Defibrillator (WCD) system to wear until an ICD is implanted. Early versions of such systems were called wearable cardiac defibrillator systems. A WCD system typically includes a harness, vest, belt, or other garment that the patient wears. The WCD system further includes electronic components, such as a defibrillator and electrodes, coupled to the harness, vest, or another garment. When the patient wears the WCD system, the electrodes may electrically contact the patient's skin, and aid in sensing the patient's electrocardiogram (ECG). If a shockable heart arrhythmia (e.g., ventricular fibrillation or VF) is detected from the ECG, then the defibrillator delivers an appropriate electric shock through the patient's body, and thus through the heart. The delivered shock may restart the patient's heart and save the patient's life.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure describes instances and examples of cardiac monitoring systems (e.g., WCD systems), devices, systems, storage media that may store programs, and methods.

In one embodiment, a method to alert a user of a wearable cardioverter defibrillator (WCD) is described. The method includes detecting a condition requiring attention of the patient and issuing an alert to notify the patient of the condition. The method also includes receiving a first input from the patient to replay the audible portion of the alert and replaying the audible portion of the alert when the first input is received.

In one embodiment, the condition may include a status of the WCD. In another embodiment, the condition may include a health status of the patient. In some embodiments, the method may include receiving a second input from the patient to silence an audible portion of the alert for a predetermined period of time. In some embodiments, the predetermined period of time may be greater than ten minutes.

In some embodiments, the method may include receiving the first input from the patient to replay the audible portion of the alert after the alert has become inactive and replaying the audible portion of the alert after the alert is inactive. In some embodiments, the method may include determining the condition has been resolved and playing a second audible alert immediately after the first audible alert to notify the patient of the resolved status. When the alert consists of more than one alert, the method may include replaying the more than one alerts in an order of predetermined priority. In some embodiments, the audible component may include a sound alert and a voice alert. Replaying the audible portion may include replaying only the voice alert of the audible portion of the alert when the second input is received. In some embodiments, the method may include playing a status alert message prior to replaying the audible portion of the alert.

In another embodiment, a wearable cardiac defibrillator (WCD) system for monitoring health of a patient wearing the WCD system is described. The system includes a support structure configured to be worn by a patient and an electronics module configured to be coupled to the support structure. The system also includes one or more processors in communication with the electronic module. The one or more processors configured to cause the system to detect a condition requiring attention of the patient and issue an alert to notify the patient of the condition. The one or more processors may cause the system to receive a first input from the patient to replay the audible portion of the alert and replay the audible portion of the alert when the first input is received.

In one embodiment, the condition may include a status of the WCD. In another embodiment, the condition may include a health status of the patient. In some embodiments, t one or more processors may cause the system to receive a second input from the patient to silence an audible portion of the alert for a predetermined period of time. In some embodiments, the predetermined period of time may be greater than ten minutes.

In some embodiments, one or more processors may cause the system to receive the first input from the patient to replay the audible portion of the alert after the alert has become inactive and replay the audible portion of the alert after the alert is inactive. In some embodiments, one or more processors may cause the system to determine the condition has been resolved and play a second audible alert immediately after the first audible alert to notify the patient of the resolved status. When the alert consists of more than one alert, the one or more processors may cause the system to replay the more than one alerts in an order of predetermined priority. In some embodiments, the audible component may include a sound alert and a voice alert. Replaying the audible portion may include replaying only the voice alert of the audible portion of the alert when the second input is received. In some embodiments, one or more processors may cause the system to play a status alert message prior to replaying the audible portion of the alert.

In another embodiment, a wearable cardiac defibrillator (WCD) system for monitoring health of a patient wearing the WCD system is described. The system includes a support structure configured to be worn by a patient and an electronics module configured to be coupled to the support structure. The system includes one or more displays proximate the electronics module and one or more processors in communication with the electronic module. The one or more processors are configured to cause the system to detect a condition requiring attention of the patient and issue an alert to notify the patient of the condition. The one or more processors are configured to cause the system to receive a first input from the patient to silence an audible portion of the alert for a predetermined period of time and receive a second input from the patient to replay the audible portion of the alert. The one or more processors are configured to cause the system to play a status alert message prior to replaying the audible portion of the alert and replay the audible portion of the alert when the second input is received

BRIEF DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed.

In the following description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

The present description includes examples of cardiac monitoring and treatment systems, such as a Wearable Cardiac Defibrillator (WCD) system, as well as alert management systems and methods. The disclosure will discuss a WCD but it will be understood that other systems can be used instead of a WCD.

Embodiments of wearable health monitoring systems include wearable ECG monitors, wearable vital sign monitoring systems, including temperature, blood pressure monitors, heart rate monitors, SPO2 detectors, step detectors, infusion pumps, etc. In some scenarios such systems can be utilized alone or in combination with other devices and/or systems. Furthermore, such devices and/or systems can be supported by accessories, which can assist with data collection, transfer, trending as well as alerts. Such accessories can include tablets, mobile devices such as a cell phone or a watch.

Wearable Cardioverter Defibrillators (WCDs) are worn by patients at risk for sudden cardiac arrest. The WCD may use alarms to inform users of equipment and/or physiological conditions that require their attention. However, the WCD is typically worn at all times, including during activities of daily. Having alarms constantly beeping and being announced while in public or among guests, or in quiet situations such as libraries, may not be desirable. The auditory emissions may disrupt the person and their surroundings.

Therefore, the WCD may be able to silence audible alarms. The visual alarm may still be active and notify the patient, but auditory alarms may be paused, quieted or all together silenced. In some instances, once an alarm is audibly silenced, the alarm may never replay again. However, it may be beneficial for a patient to hear the alarm at a later time. Therefore, the WCD may also allow the patient to replay an alarm at a later time. This may enable the patient to travel to a more appropriate setting to play the alarm. The patient may also replay alarms that they may have missed. For example, in loud environments, the patient may not have heard the alarm, but again, playing the alarm may be beneficial to the patient. Therefore, the patient may replay any messages at a later time on demand.

Figure 1:
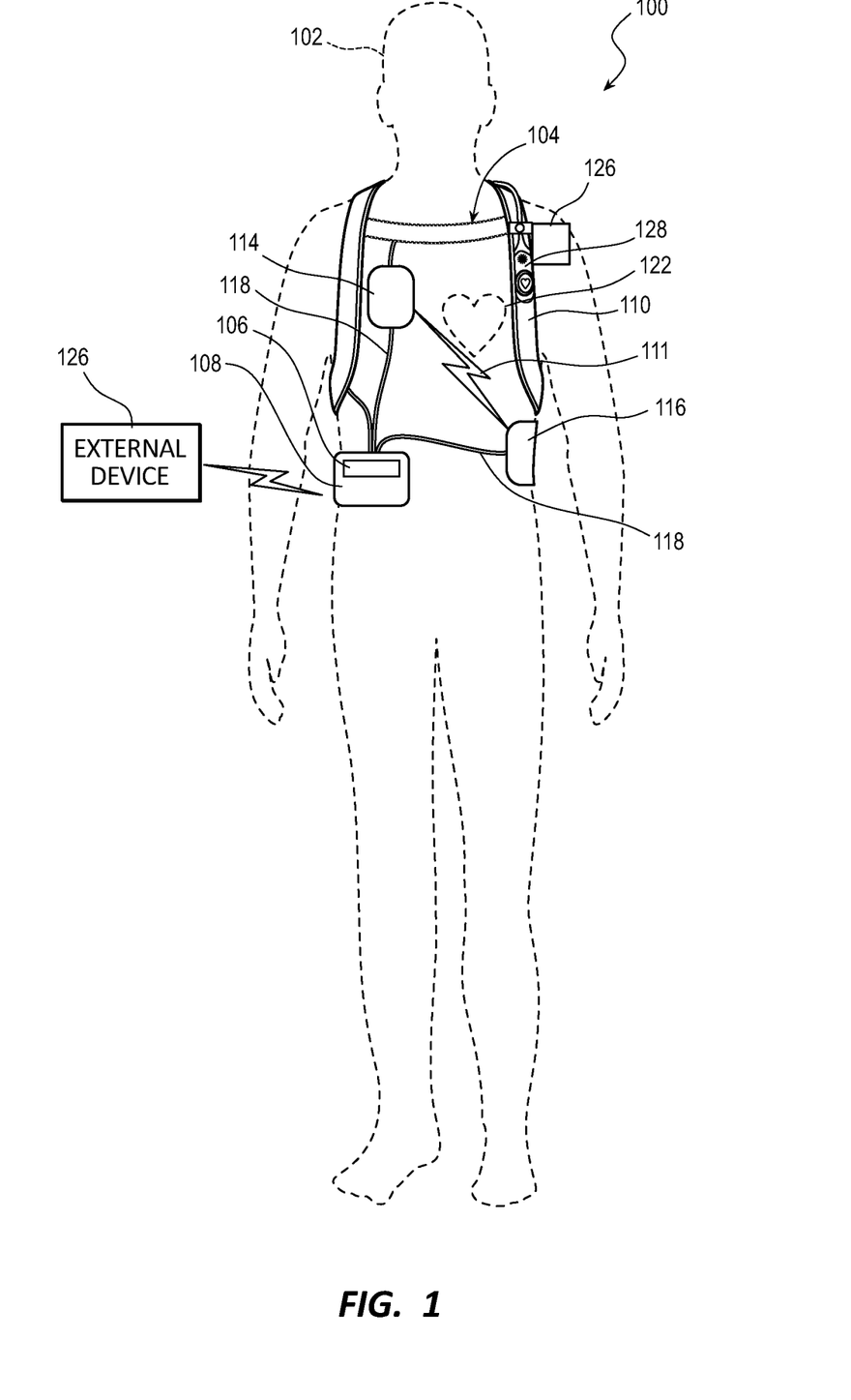
FIG. 1 is a diagram of a sample WCD system in accordance with exemplary embodiments described herein.

FIG. 1 illustrates a system 100 with a patient 102 wearing an example of a WCD system 104 according to embodiments described herein. In some embodiments, the WCD system 104 may include one or more communication devices 106, a support structure 110, and an external defibrillator 108 connected to two or more defibrillation electrodes 114, 116, among other components.

The support structure 110 may be worn by the patient 102. The patient 102 may be ambulatory, meaning the patient 102 can walk around and is not necessarily bed-ridden while wearing the wearable portion of the WCD system 104. While the patient 102 may be considered a "user" of the WCD system 104, this is not a requirement. For instance, a user of the WCD system 104 may also be a clinician such as a doctor, nurse, emergency medical technician (EMT) or other similarly tasked individual or group of individuals. In some cases, a user may even be a bystander. The particular context of these and other related terms within this description should be interpreted accordingly.

In some embodiments, the support structure 110 may include a vest, shirt, series of straps, or other system enabling the patient 102 to carry at least a portion of the WCD system 104 on the patient's body. In some embodiments, the support structure 110 may comprise a single component. For example, the support structure 110 may comprise a vest or shirt that properly locates the WCD system 104 on a torso 112 of the patient 102. The single component of the support structure 110 may additionally carry or couple to all of the various components of the WCD system 104.

In other embodiments, the support structure 110 may comprise multiple components. For example, the support structure 110 may include a first component resting on a patient's shoulders. The first component may properly locate a series of defibrillation electrodes 114, 116 on the torso 112 of the patient 102. A second component may rest more towards a patient's hips, whereby the second component may be positioned such that the patient's hips support the heavier components of the WCD system 104. In some embodiments, the heavier components of the WCD system 104 may be carried via a shoulder strap or may be kept close to the patient 102 such as in a cart, bag, stroller, wheelchair, or other vehicle.

In some embodiments, the support structure 110 can be worn by being attached to the body of the patient 102 by adhesive material, for example as shown and described in U.S. Pat. No. 8,024,037, incorporated herein in its entirety by reference. In some embodiments, the support structure 110 can be implemented as described in U.S. Patent Publication No. 20170056682, incorporated herein in its entirety by reference. In still further embodiments, additional components of the WCD system 104 may incorporated in the housing of the support structure 110 instead of being attached externally to the support structure 110. One example is described in U.S. Patent Publication No. 20170056682, incorporated herein in its entirety by reference.

The external defibrillator 108 may be coupled to the support structure 110 or may be carried remotely from the patient 102. The external defibrillator 108 may be triggered to deliver an electric shock to the patient 102 when patient 102 wears the WCD system 104. For example, if certain thresholds are exceeded or met, the external defibrillator 108 may engage and deliver a shock to the patient 102.

The defibrillation electrodes 114, 116 can be configured to be worn by patient 102 in a number of ways. For instance, the defibrillator 108 and the defibrillation electrodes 114, 116 can be coupled to the support structure 110 directly or indirectly. For example, the support structure 110 can be configured to be worn by the patient 102 to maintain at least one of the electrodes 114, 116 on the body of the patient 102, while the patient 102 is moving around, etc. The electrodes 114, 116 can be thus maintained on the torso 112 by being attached to the skin of patient 102, simply pressed against the skin directly or through garments, etc. In some embodiments, the electrodes 114, 116 are not necessarily pressed against the skin but becomes biased that way upon sensing a condition that could merit intervention by the WCD system 104. In addition, many of the components of defibrillator 108 can be considered coupled to support structure 110 directly, or indirectly via at least one of defibrillation electrodes 114, 116.

The WCD system 104 may defibrillate the patient 102 by delivering an electrical charge, pulse, or shock 111 to the patient 102 through a series of electrodes 114, 116 positioned on the torso 112. For example, when defibrillation electrodes 114, 116 are in good electrical contact with the torso 112 of patient 102, the defibrillator 108 can administer, via electrodes 114, 116, a brief, strong electric pulse 111 through the body. The pulse 111 is also known as shock, defibrillation shock, therapy, electrotherapy, therapy shock, etc. The pulse 111 is intended to go through and restart heart 122, in an effort to save the life of patient 102. The pulse 111 can further include one or more pacing pulses of lesser magnitude to pace heart 122 if needed. The electrodes 114, 116 may be electrically coupled to the external defibrillator 108 via a series of electrode leads 118. The defibrillator 108 may administer an electric shock 111 to the body of the patient 102 when the defibrillation electrodes 114, 116 are in good electrical contact with the torso 112 of patient 102. In some embodiments, devices (not shown) proximate the electrodes 114, 116 may emit a conductive fluid to encourage electrical contact between the patient 102 and the electrodes 114, 116.

In some embodiments, the WCD system 104 may also include either an external or internal monitoring device or some combination thereof. FIG. 1 displays an external monitoring device 124 which may also be known as an outside monitoring device. The monitoring device 124 may monitor at least one local parameter. Local parameters may include a physical state of the patient 102 such as ECG, movement, heartrate, pulse, temperature, and the like. Local parameters may also include a parameter of the WCD 104, environmental parameters, or the like. For example, in some embodiments, the monitoring device 124 may include sensors to gather patient movement, ambient lighting, and the like. The monitoring device 124 may be physically coupled to the support structure 110 or may be proximate the support structure 110. In either location, the monitoring device 124 is communicatively coupled with other components of the WCD 104.

For some of these parameters, the device 124 may include one or more sensors or transducers. Each one of such sensors can be configured to sense a parameter of the patient 102, and to render an input responsive to the sensed parameter. In some embodiments, the input is quantitative, such as values of a sensed parameter; in other embodiments, the input is qualitative, such as informing whether or not a threshold is crossed. In some instances, these inputs about the patient 102 are also referred to herein as patient physiological inputs and patient inputs. In some embodiments, a sensor can be construed more broadly, as encompassing many individual sensors.

In some embodiments, a communication device 106 may enable the patient 102 to interact with, and garnish data from, the WCD system 104. The communication device 106 may enable a patient or third party to view patient data, dismiss a shock if the patient is still conscious, turn off an alarm, and otherwise engage with the WCD system 104. In some instances, the communication device 106 may transfer or transmit information include patient data to a third-party data server such as a cloud server or a blockchain server. In some embodiments, the communication device 106 may be a separable part of an external defibrillator 108. For example, the communication device 106 may be a separate device coupled to the external defibrillator 108. In some embodiments, the communication device 106 may be wired or wirelessly linked to the external defibrillator 108 and may be removable from the defibrillator 108. In other embodiments, the communication device 106 may form an inseparable assembly and share internal components with the external defibrillator 108. In some embodiments, the WCD system 104 may include more than one communication device 106. For example, the defibrillator 108 may include components able to communicate to the patient and the WCD system 104 may include a separate communication device 106 remote form the defibrillator 108.

In some embodiments, the communication device 106 may be communicatively coupled to an alert button 128. The alert button 128 may be removably coupled to the support structure 110. The patient 102 may couple the alert button 128 to the support structure 110 or may couple the alert button 128 to an article of clothing. The alert button 128 may have a wired connection or be wirelessly connected to the communication device 106. In some embodiments, the alert button 128 may include a visual output, an audio output, and a user input. The visual output may include a light, such as an LED, a small screen, or some combination thereof. Likewise, the audio output may include one or more speakers. The output of the audio output may be loud enough to be heard over nominal background noise. In some embodiments, the audio output might have an adjustable volume range. In some embodiments, the alert button 128 may include a microphone. In still further embodiments, the alert button 128 may also include a haptic response.

In some embodiments, the defibrillator 108 may connect with one or more external devices 126. For example, as shown in FIG. 1, the defibrillator 108 may connect to various external devices 126 such as the cloud, a remote desktop, a laptop, a mobile device, or other external device using a network such as the Internet, local area networks, wide area networks, virtual private networks (VPN), other communication networks or channels, or any combination thereof.

In embodiments, one or more of the components of the exemplary WCD system 104 may be customized for the patient 102. Customization may include a number of aspects including, but not limited to, fitting the support structure 110 to the torso 112 of patient 102; baseline physiological parameters of patient 102 can be measured, such as the heart rate of patient 102 while resting, while walking, motion detector outputs while walking, etc. The measured values of such baseline physiological parameters can be used to customize the WCD system, in order to make its analysis more accurate, since patients' bodies differ from one another. Of course, such parameter values can be stored in a memory of the WCD system, and the like. Moreover, a programming interface can be made according to embodiments, which receives such measured values of baseline physiological parameters. Such a programming interface may input automatically in the WCD system these, along with other data.

Figure 2:
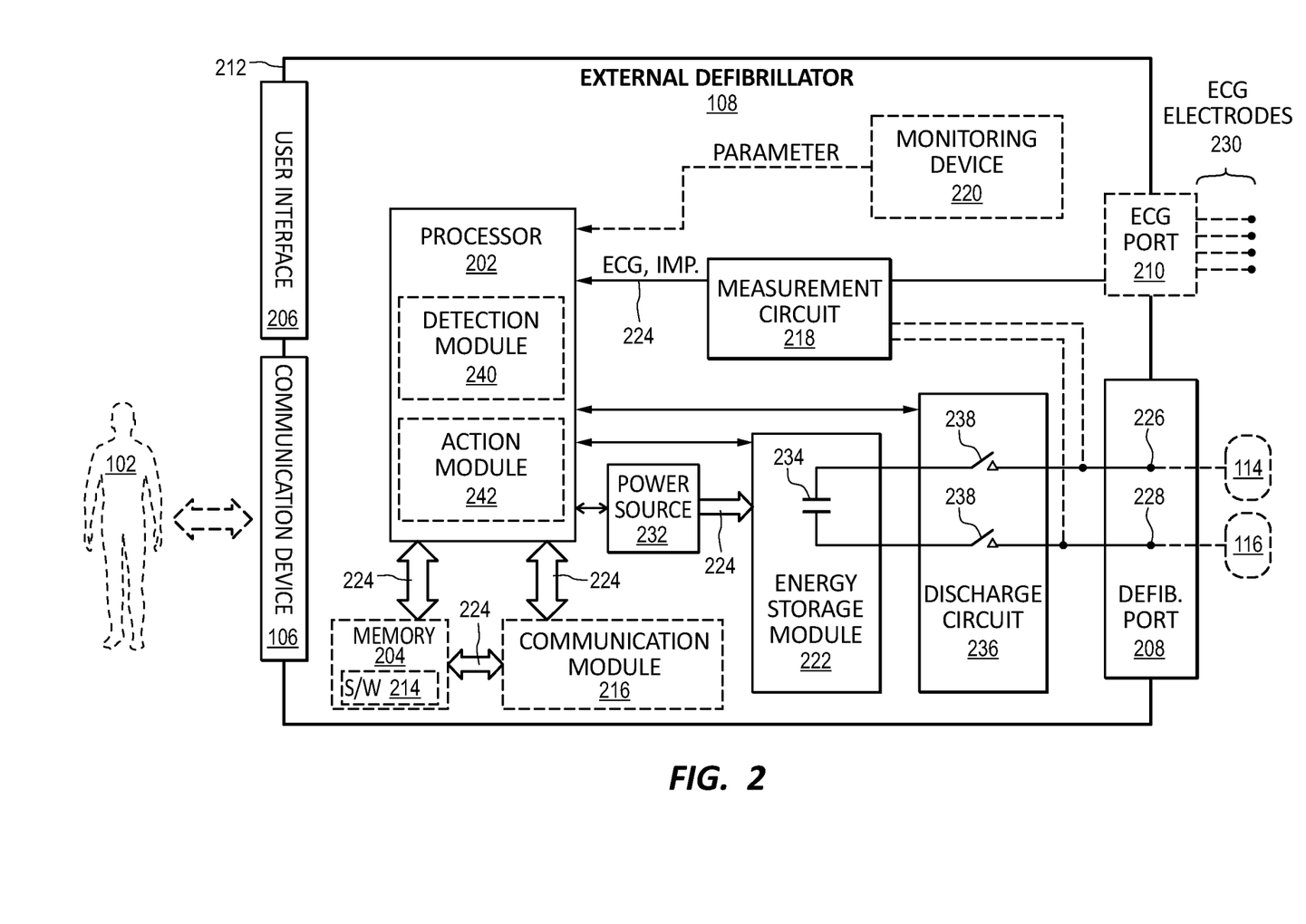
FIG. 2 is a block diagram of an example defibrillator in accordance with exemplary embodiments described herein.

FIG. 2 is a diagram displaying various components of an example external defibrillator 108. The external defibrillator 108 may be an example of the defibrillator 108 described with reference to FIG. 1. The components shown in FIG. 2 may be contained within a single unit or may be separated amongst two or more units in communication with each other. The defibrillator 108 may include a communication device 106, processor 202, memory 204, defibrillation port 208, and ECG port 210, among other components. In some embodiments, the components are contained within a housing 212 or casing. The housing 212 may comprise a hard shell around the components or may comprise a softer shell for increased patient comfort.

The communication device 106, processor 202, memory 204 (including software/firmware code (SW) 214), defibrillation port 208, ECG port 210, communication module 216, measurement circuit 218, monitoring device 220, and energy storage module 222 may communicate, directly or indirectly, with one another via one or more buses 224. The one or more buses 224 may allow data communication between the elements and/or modules of the defibrillator 108.

The memory 204 may include random access memory (RAM), read only memory (ROM), flash RAM, and/or other types. The memory 204 may store computer-readable, computer-executable software/firmware code 214 including instructions that, when executed, cause the processor 202 to perform various functions (e.g., determine shock criteria, determine heart rate, issue shock command, issue alerts, etc.). In some embodiments, the processor 202 may include an intelligent hardware device, e.g., a central processing unit (CPU), a microcontroller, an application-specific integrated circuit (ASIC), etc.

In some embodiments, the memory 204 can contain, among other things, the Basic Input-Output system (BIOS) which may control basic hardware and/or software operations such interactions and workings of the various components of the defibrillator 108, and in some embodiments, components external to the defibrillator 108. For example, the memory 204 may contain various modules to implement the workings of the defibrillator 108 and other aspects of the present disclosure.

In some embodiments, the defibrillator 108 may include a user interface 206. The user interface 206 may be in addition to or part of the communication device 106. The user interface 206 may display an ECG of the patient, a status of the defibrillator 108, a status of a charge (e.g., a battery charge or an energy storage module), and the like.

In some embodiments, the user interface 206 may include output devices, which may include visual, audible, or tactile, for communicating to a user by outputting images, sounds or vibrations. Images, sounds, vibrations, and an alert or notification that can be perceived by a person is also called human-perceptible indications (HPIs). Output devices, or HPIs, may include a light(s), a screen to display what is sensed, detected and/or measured, speakers, and the like. In some embodiments, the screen may provide visual feedback to a third party for their resuscitation attempts and treatment plans. In some embodiments, the speaker may be configured to issue voice prompts, beeps, loud alarm sounds and/or words to warn bystanders, etc.

In some embodiments, the user interface 206 may further include input devices for receiving inputs from users. Such input devices may include various controls, such as push-buttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

In some embodiments, the defibrillator 108 may include a defibrillation port 208. The defibrillation port 208 may comprise a socket, opening, or electrical connection in the housing 212. In some instances, the defibrillation port 208 may include two or more nodes 226, 228. The two or more nodes 226, 228 may accept two or more defibrillation electrodes (e.g., defibrillation electrodes 114, 116, FIG. 1). The nodes 226, 228 may provide an electrical connection between the defibrillation electrodes 114, 116 and the defibrillator 108. The defibrillation electrodes 114, 116 may plug into the two or more nodes 226, 228 via one or more leads (e.g., leads 118), or, in some instances, the defibrillation electrodes 114, 116 may be hardwired to the nodes 226, 228. Once an electrical connection is established between the defibrillation port 208 and the electrodes 114, 116, the defibrillator 108 may be able to deliver an electric shock to the patient 102.

In some embodiments, the defibrillator 108 may include an ECG port 210 in the housing 212. The ECG port 210 may accept one or more ECG electrodes 230 or ECG leads. In some instances, the ECG electrodes 230 sense a patient's ECG signal. For example, the ECG electrodes 230 may record electrical activity generated by heart muscle depolarization, timing, or both. The ECG electrodes 230 may utilize 4-leads to 12-leads or multichannel ECG, or the like. The ECG electrodes 230 may connect with the patient's skin.

In some embodiments, the defibrillator 108 may include a measurement circuit 218. The measurement circuit 218 may be in communication with the ECG port 210. For example, the measurement circuit 218 may receive physiological signals from ECG port 210. The measurement circuit 218 may additionally or alternatively receive physiological signals via the defibrillation port 208 when defibrillation electrodes 114, 116 are attached to the patient 102. The measurement circuit 218 may determine a patient's ECG signal from a difference in voltage between the defibrillation electrodes 114, 116.

In some embodiments, the measurement circuit 218 may monitor the electrical connection between the defibrillation electrodes 114, 116 and the skin of the patient 102. For example, the measurement circuit 218 can detect impedance between electrodes 114, 116. The impedance may indicate the effective resistance of an electric circuit. An impedance calculation may determine when the electrodes 114, 116 have a good electrical connection with the patient's body.

If, in some embodiments, the defibrillator 108 lacks a sensor port, the measurement circuit 218 may obtain physiological signals through nodes 226, 228 when defibrillation electrodes 114, 116 are attached to the patient. The input may reflect an ECG measurement. The patient parameter can be an ECG, which can be sensed as a voltage difference between electrodes 114, 116. In addition, the patient parameter may be an impedance, which may be sensed between electrodes 114, 116 and/or between the connections of sensor port considered pairwise. In some embodiments, the impedance may be used to determine when electrodes 114, 116 and/or sensing electrodes are not making good electrical contact with the patient's body.

In some embodiments, the defibrillator 108 may include an internal monitoring device 220 within the housing 212. The monitoring device 220 may monitor at least one local parameter. Local parameters may include physical state of the patient such as ECG, movement, heartrate, pulse, temperature, and the like. Local parameters may also include a parameter of the WCD system (e.g., WCD 104, FIG. 1), defibrillator 108, environmental parameters, or the like.

In some embodiments, the WCD system 104 may include an internal monitoring device 220 and an external monitoring device (e.g., external monitoring device 124). If both monitoring devices 124, 220 are present, the monitoring devices 124, 220 may work together to parse out specific parameters depending on position, location, and other factors. For example, the external monitoring device 124 may monitor environmental parameters while the internal monitoring device 220 may monitor patient and system parameters.

Patient parameters may include patient physiological parameters. Patient physiological parameters may the WCD system in detecting when the patient is in need of a shock or other intervention or assistance. Patient physiological parameters may also include the patient's medical history, event history, and the like. Examples of such parameters may include the patient's ECG, blood oxygen level, blood flow, blood pressure, blood perfusion, pulsatile change in light transmission or reflection properties of perfused tissue, heart sounds, heart wall motion, breathing sounds and pulse.

The internal and external monitoring devices 220, 124 may include one or more sensors configured to acquire patient physiological signals. For example, either one or both monitoring devices 220, 124 may include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on.

In some embodiments, the local parameter is a trend that can be detected in a monitored physiological parameter of patient. A trend can be detected by comparing values of parameters at different times over short and long terms. Parameters whose detected trends can particularly help a cardiac rehabilitation program may include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2, CO2, or other parameters such as those mentioned above, f) respiratory function, respiratory rate, etc.; g) motion, level of activity; and so on. Once a trend is detected, it can be stored and/or reported via a communication link, along perhaps with a warning if warranted. The report may aid a physician in monitoring the progress of patient.

In some embodiments, the monitoring devices 220, 124 may include sensors that monitor external conditions. For example, the monitoring devices may monitor environmental parameters. Environmental parameters may include ambient temperature, pressure, humidity, and the like.

In some embodiments, the defibrillator 108 may include a power source 232. The power source 232 may comprise a battery or battery pack, which may be rechargeable. In some instances, the power source 232 may comprise a series of different batteries to ensure the defibrillator 108 has power. For example, the power source 232 may include a series of rechargeable batteries as a prime power source and a series of non-rechargeable batteries as a secondary source. If the patient 102 is proximate an AC power source, such as when sitting down, sleeping, or the like, the power source 232 may include an AC override wherein the power source 232 draws power from the AC source.

In some embodiments, the defibrillator 108 may include an energy storage module 222. The energy storage module 222 may store electrical energy in preparation or anticipation of providing a sudden discharge of electrical energy to the patient. In some embodiments, the energy storage module 222 may have its own power source and/or battery pack. In other embodiments, the energy storage module 222 may pull power from the power source 232. In still further embodiments, the energy storage module 222 may include one or more capacitors 234. The one or more capacitors 234 may store an electrical charge, which may be administered to the patient. The processor 202 may be communicatively coupled to the energy storage module 222 to trigger the amount and timing of electrical energy to provide to the defibrillation port 208 and, subsequently, the patient 102.

In some embodiments, the defibrillator 108 may include a discharge circuit 236. The discharge circuit 236 may control the energy stored in the energy storage module 222. For example, the discharge circuit 236 may either electrical couple or decouple the energy storage module 222 to the defibrillation port 208. The discharge circuit 236 may be communicatively coupled to the processor 202 to control when the energy storage module 222 and the defibrillation port 208 should or should not be coupled to either administer or prevent a charge from emitting from the defibrillator 108. In some embodiments, the discharge circuit 236 may include on or more switches 238. In further embodiments, the one or more switches 238 may include an H-bridge.

In some embodiments, the defibrillator 108 may include a communication module 216. The communication module 216 may establish one or more communication links with either local hardware and/or software to the WCD system 104 and defibrillator 108 or to remote hardware separate from the WCD system 104. In some embodiments, the communication module 216 may include one or more antennas, processors, and the like. The communication module 216 may communicate wirelessly via radio frequency, electromagnetics, local area networks (LAN), wide area networks (WAN), virtual private networks (VPN), RFID, Bluetooth, cellular networks, and the like. The communication module 216 may facilitate communication of data and commands such as patient data, episode information, therapy attempted, CPR performance, system data, environmental data, and so on. In some embodiments, the communication module 216 may include a display screen to display messages to the patient. In some embodiments, the display screen may be a touch screen, backlit screen, passive, reflective LCD screen or the like.

In further embodiments, the communication module 216 may include one or more LEDs which may also be used to convey information to the patient. In some embodiments, the LED brightness may be modulated, the LEDs may be color changing, and the like. In some embodiments, if multiple LEDs are present, each LED may represent various bits of information. For example, one LED may represent heartrate information and enable the patient to quickly determine their heart is operating normally. Another LED may represent the heartrate signal to ensure the patient the heartrate readings are being properly transmitted. Another LED may also represent system status and allow the patient to easily ascertain that the system is fully functioning.

In some embodiments, the processor 202 may execute one or more modules. For example, the processor 202 may execute a detection module 240 and/or an action module 242. The detection module 240 may be a logic device or algorithm to determine if any or a variety of thresholds are exceeded which may require action of the defibrillator 108. For example, the detection module 240 may receive and interpret all of the signals from the ECG port 210, the defibrillation port 208, the monitoring device 220, an external monitoring device, and the like. The detection module 240 may process the information to ensure the patient is still conscious and healthy. If any parameter indicates the patient 102 may be experiencing distress or indicating a cardiac episode, the detection module 240 may activate the action module 242.

The action module 242 may receive data from the detection module 240 and perform a series of actions. For example, an episode may merely be a loss of battery power at the power source 232 or the energy storage module 222, or one or more electrodes (e.g., ECG electrodes, defibrillation electrodes) may have lost connection. In such instances, the action module 242 may trigger an alert to the patient or to an outside source of the present situation. This may include activating an alert module. If an episode is a health risk, such as a cardiac event, the action module 242 may begin a series of steps. This may include issuing a warning to the patient, issuing a warning to a third party, priming the energy storage module 222 for defibrillation, releasing one or more conductive fluids proximate defibrillation electrodes 114, 116, and the like.

Figure 3:
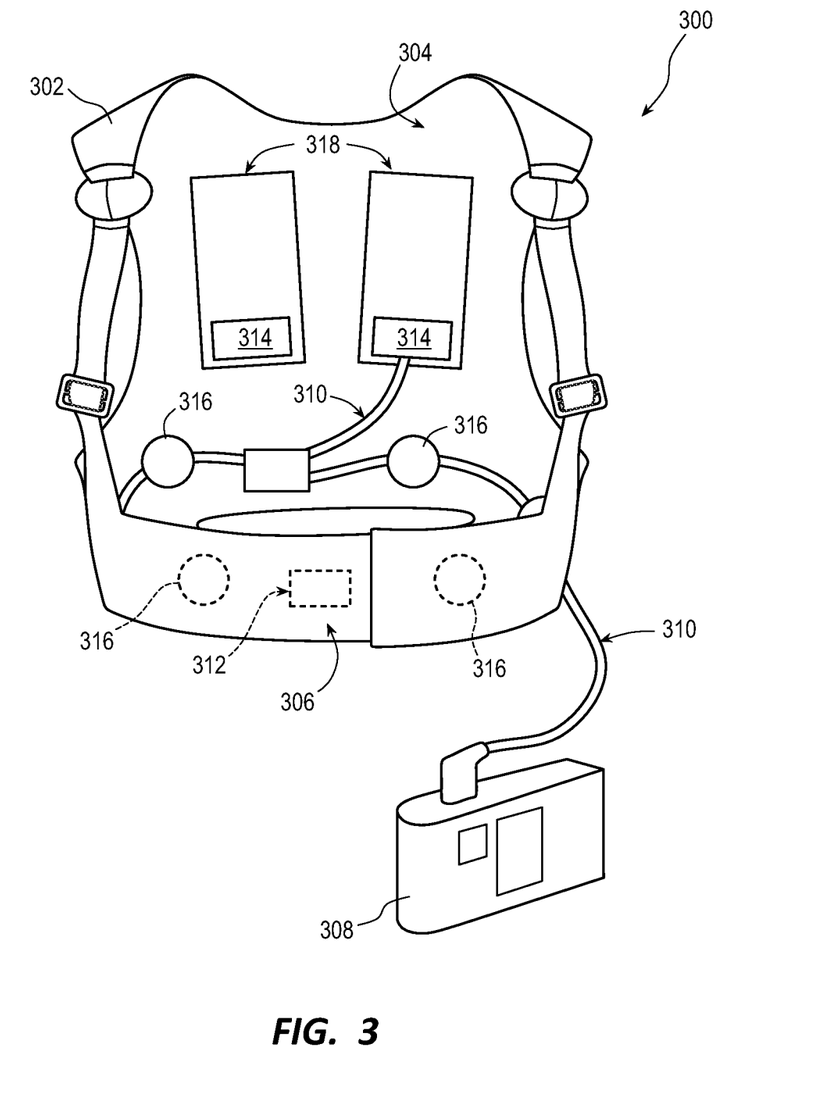
FIG. 3 is a diagram of sample embodiments of components of a WCD system in accordance with exemplary embodiments described herein.

FIG. 3 is a diagram of sample embodiments of components of a WCD system 300 according to exemplary embodiments. The WCD system 300 may be an example of the WCD system 104 describe with reference to FIG. 1. In some embodiments, the WCD system 300 may include a support structure 302 comprising a vest-like wearable garment. In some embodiments, the support structure 302 has a back side 304, and a front side 306 that closes in front of a chest of the patient.

In some embodiments, the WCD system 300 may also include an external defibrillator 308. The external defibrillator 308 may be an example of the defibrillator 108 describe with reference to FIGS. 1 and 2. As illustrated, FIG. 3 does not show any support for the external defibrillator 308, but as discussed, the defibrillator 308 may be carried in a purse, on a belt, by a strap over the shoulder, and the like as discussed previously. One or more wires 310 may connect the external defibrillator 308 to one or more electrodes 312, 314, 316. Of the connected electrodes, electrodes 312, 314 are defibrillation electrodes, and electrodes 316 are ECG sensing electrodes.

The support structure 302 is worn by the patient to maintain electrodes 312, 314, 316 on a body of the patient. For example, the back-defibrillation electrodes 314 are maintained in pockets 318. In some embodiments, the inside of the pockets 318 may comprise loose netting, so that the electrodes 314 can contact the back of the patient. In some instances, a conductive fluid may be deployed to increase connectivity. Additionally, in some embodiments, sensing electrodes 316 are maintained in positions that surround the patient's torso, for sensing ECG signals and/or the impedance of the patient.

In some instances, the ECG signals in a WCD system 300 may comprise too much electrical noise to be useful. To ameliorate the problem, multiple ECG sensing electrodes 316 are provided, for presenting many options to the processor (e.g., processor 202, FIG. 2). The multiple ECG sensing electrodes 316 provide different vectors for sensing the ECG signal of the patient.

Figure 4:
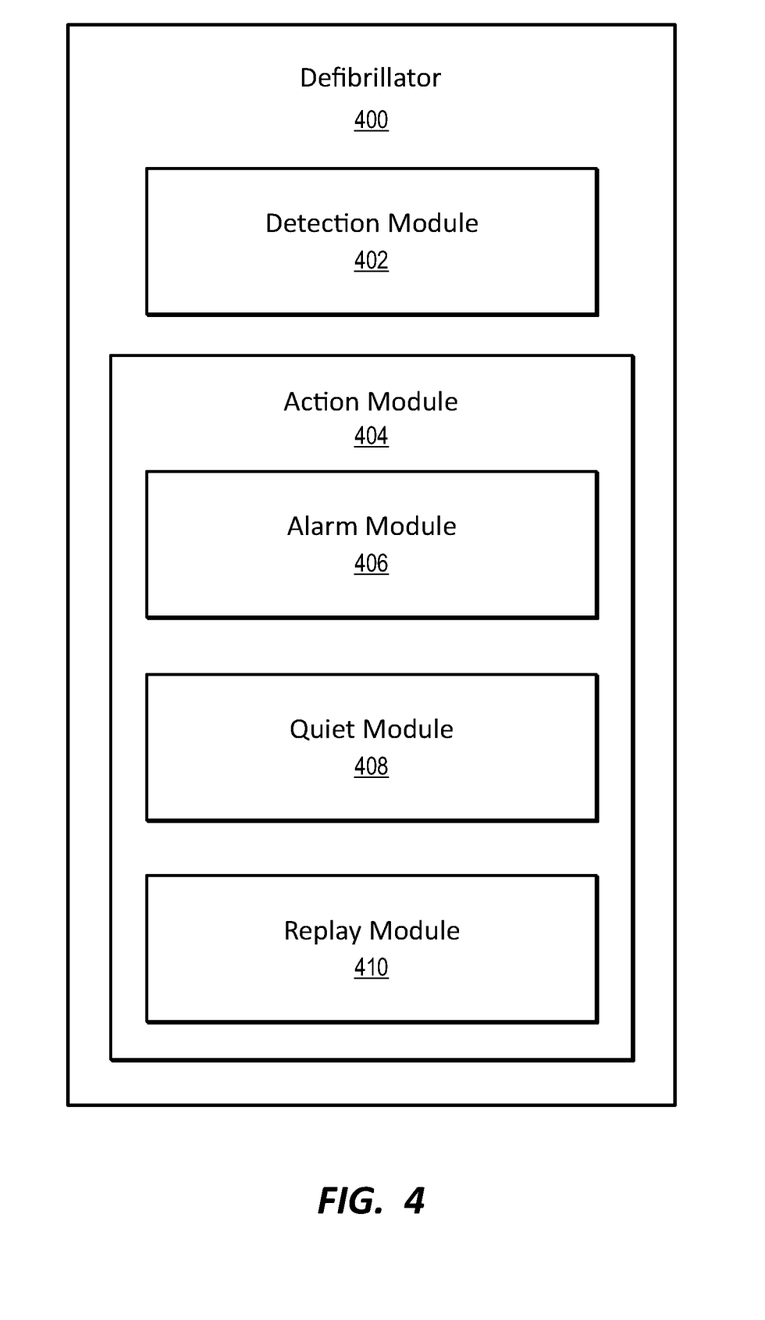
FIG. 4 is a block diagram of an example defibrillator in accordance with exemplary embodiments described herein.

FIG. 4 is a block diagram illustrating components of one example of a defibrillator 400. The defibrillator 400 may be an example of the defibrillator 108 described with reference to FIGS. 1 and 2 and defibrillator 308 described with reference to FIG. 3. In this example, the defibrillator 400 has a detection module 402 and an action module 404. The detection module 402 and action module 404 may be examples of the detection module 240 and action module 242 described with reference to FIG. 2. In some embodiments, the action module 404 may include a heart rate (HR) analysis module 406, a consistency module 408, and shock determination module 410.

The detection module 402 may aid in the detection of various shockable conditions. For example, the detection module 402 may receive a signal from at least one electrode and analyze the signal for a heart rate and other indicators of an abnormal heart condition. If a shockable or monitoring condition exists, the detection module 402 may communicate the need for action to the action module 404.

In some embodiments, the detection module 402 may also detect system conditions. For example, the detection module 402 may determine a battery status of the defibrillator. This may enable the detection module 402 to issue an alert when the battery status is below an acceptable threshold. The detection module 402 may also monitor a status of the electrodes to determine if the electrodes are properly secured to the patient and the leads are all functioning appropriately. The detection module 402 may also track a status of the various other components of the WCD system, such as the alert button, remote monitoring device, and the like. The detection module 402 may track conditions of the defibrillator itself. For example, the detection module 402 may detect device orientation, movement, external forces, and the like.

In some embodiments, the detection module 402 may also detect ambient and external conditions. For example, the detection module 402 may detect environmental conditions such as noise levels, lighting levels, weather conditions, and the like. The detection module 402 may monitor time of day, in some embodiments, the detection module 402 may monitor the patient's habits through the day and days of the week. In some embodiments, the detection module 402 may begin to detect and track patient's habits to determine if the patient is acting within their normal routine or if an abnormal lack or increase in activity, including heart activity, is occurring.

In some embodiments, based at least in part on information and data from the detection module 402, the action module 404 may take one or more actions. For example, in some embodiments, the action module 404 may have an alarm module 406, a display module 408, and a replay module 410.

The alarm module 406 may cause one or more alarms to issue. For example, the alarm module 406 may cause a safety alarm, a physiological alarm, a system alarm, or any other alarm related to the WCD to issue. The alarm may have multiple components. For example, the alarm may have a multi-visual component, an audible component, and a haptic component. The multi-visual component may include a light(s), a visual display including a GUI, or some combination thereof. The visual component may use the light(s) to garnish the attention of the user and may display a written message or coded message on a screen.

In some embodiments, the alarm module 406 may cause an audible alarm to issue. The audible alarm may be an alert or may be a spoken alarm relaying a message concerning the WCD or patient condition. The alert may be a pre-programmed noise such as a jingle, ping, or other alarm. Various conditions or severity of alerts may have different noises. For example, emergency alerts may have an audible alert more closely resembling an emergency alarm. Conditions alerts may have other noises that are less severe.

Spoken alarms may announce the alert or simply provide a spoken alarm that an alert is pending. In some embodiments, the patient may have the option to have a longer description spoken and/or trouble shooting options. The audible alarms, including spoken alarms, may also have varying volumes. For example, more urgent alarms may have a higher decibel output. These type of emergency alarms may not be muted or silenced. The spoken alarms may, in some embodiments, warn of an impending shock.

In some embodiments, the alarms may all work conjunctively. For example, as an audible alert is being spoken and sounded, the visual display may provide a written description of the alert and a lighted display may also be active. In further embodiments, depending on the severity of the alert, not all alert notifications may be triggered. For example, a low battery alert may simple include a visual component. As the battery becomes dangerously low, the alert may escalate to a more urgent alert to ensure proper WCD functionality.

In some embodiments, the feedback module 410 may provide user feedback based on a variety of conditions. For example, the feedback module 410 may provide positive feedback to the user. In some embodiments, the positive feedback may assure the assure that the WCD system and the defibrillator 400 are operating properly. This may include offering positive feedback when an issue has been resolved. The feedback module 410 may increase a confidence of the user in system behavior by actively informing the user when an issue is resolved or when the system is properly operating. In some embodiments, the feedback module 410 may provide feedback by emitting a tone, emitting a vibration pattern, displaying content on the screen, using LEDs with specific patterns, or some combination thereof. The specific feedback mechanism may change based on the specific issue resolution, system status, or the like.

In some embodiments, the defibrillator may include a quiet module 408. The quiet module 408 may allow the user to silence or delay audible messages. For example, in some embodiments, the user may wish for any audible alarms to be silent. The quiet module 408 may enable the user to adjust the volume of the audible alarms, including silencing them, to reduce interruptions. In some embodiments, the quiet module 408 may allow the user to silence alarms for a predetermined time period. For example, the quiet module 408 may silence alarms for a snooze period such as 30 seconds to six minutes. The quiet module 408 may also prolong a snooze for 30 minutes to an hour. In some embodiments, the quiet module 408 may last for longer durations, such as an hour or longer or sometimes overnight. This may prevent the defibrillator 400 from waking the patient during the night.

In some embodiments, the defibrillator 400 may also include a replay module 410. The replay module 410 may allow the user to cause the voice prompt or voice message to play again on demand. This may allow the user to hear the message when it's convenient for them rather than missing the message or waiting for the system to replay the message. The replay module 410 may respond to one or more user inputs to replay the message. This may include a voice command, an input button, a screen input, or some other input method to prompt the replay module 410 to play the message. In some embodiments, if more than one message was missed, the replay module 410 may replay all messages and automatically play the message in order of importance. In other embodiments, the user may be able to select the messages to replay and dismiss the messages that they do not wish to hear.

Figure 5:
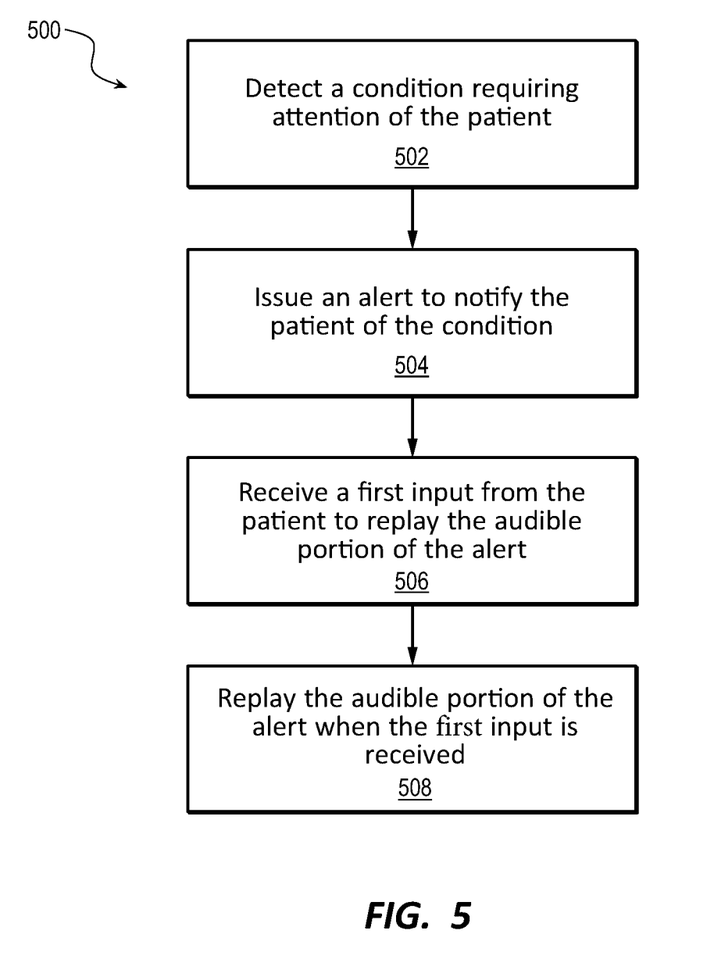
FIG. 5 is a flow diagram in accordance with exemplary embodiments described herein.

FIG. 5 is a flow chart illustrating an example of a method 500 for WCD systems, in accordance with various aspects of the present disclosure. For clarity, the method 500 is described below with reference to aspects of one or more of the systems described herein.

At block 502, the method 500 may detect a condition requiring the attention of the patient. The condition may be a health condition such as a heart condition. The condition may be some other physiological condition such as low blood flow, low heart rate, low blood pressure, high blood pressure, or the like. In some embodiments, the condition may be preemptive signs of a heart attack.

In other embodiments, the condition may be a system condition. For example, the system may be experiencing increased noise or the electrodes may be disconnected. The defibrillation pads may have come off the patient's skin. The defibrillator battery may be low. The WCD system may require service.

At block 504, the method 500 may issue an alert to notify the patient of the condition. In some embodiments, the alert may comprise multiple components. For example, the alert may include an audible component and a visual component. In some embodiments, the alert may also incorporate a haptic component. In some instances, the audible component may comprise an alarm sound or jingle as well as a voice alert. In some instances, the visual component may comprise multiple parts as well. For example, the visual component may comprise a flashing alert as well as a graphical interface for written or imagery messages.

At block 506, the method 500 may receive a first input from the patient to replay the audible portion of the alert. For example, the patient may depress a button or otherwise input to the defibrillator and/or WCD system that they wish to rehear the voice alert. At block 508, the method 500 may replay the audible portion of the alert when the first input is received. In some embodiment, the method 500 may only replay the voice alert portion of the audible alert.

Thus, the method 500 may provide for one method of replaying to a user of a WCD system. It should be noted that the method 500 is just one implementation and that the operations of the method 500 may be rearranged or otherwise modified such that other implementations are possible.

Figure 6:
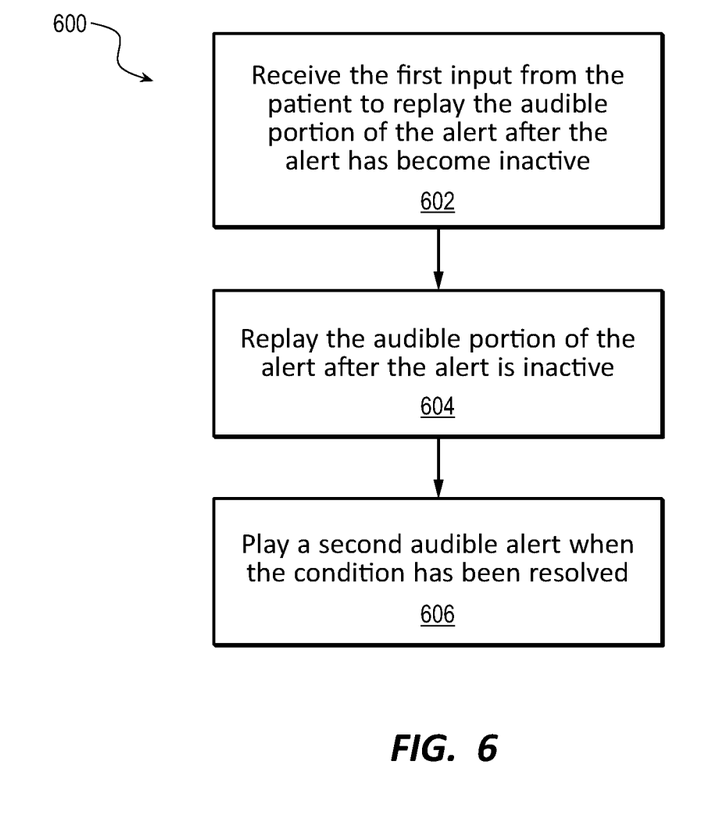
FIG. 6 is a flow diagram in accordance with exemplary embodiments described herein.

FIG. 6 is a flow chart illustrating an example of a method 600 for WCD systems, in accordance with various aspects of the present disclosure. For clarity, the method 600 is described below with reference to aspects of one or more of the systems described herein.

At block 602, the method 600 may receive the first input from the patient to replay the audible portion of the alert after the alert has become inactive. For example, the alerts may only be active for a predetermined period of time. The predetermined period of time may comprise a time threshold (e.g., ten minutes) or may be when the condition itself has expired (e.g., noise in the ECG signal). Once the alert has become inactive, or become resolved, the alert may not appear to the patient. However, if the patient has silenced an alarm or entered the WCD into a silent mode, the patient may still wish to hear alerts afterwards.

Therefore, at block 604, the method 600 may replay the audible of the alert after the alert is inactive. This may enable the patient to still gather the information concerning either their own health or the status of the WCD system during the period of time alarms were silenced.

In some embodiments, if the condition has resolved itself, but alerts were silenced, at block 606, the method 600 may play a second audible alert to notify the patient that the condition has been resolved. In some embodiments, the method 600 may play the resolution alert before the conditional alert has been replayed. For example, the resolution alert may say, "[Insert condition] has been resolved. The following alert issued while device was silenced." This may allow the user to know the condition has bene resolved and not take any action. In some embodiments, the condition may not be resolved. In those embodiments, the method 600 may preempt the alert message with a status message such as, "[Insert condition] has not been resolved. The following alert issued while device was silenced and requires attention." This may allow the patient to hear the message fully and begin to play for resolving the conditions.

Thus, the method 600 may provide for one method of replaying to a user of a WCD system. It should be noted that the method 600 is just one implementation and that the operations of the method 600 may be rearranged or otherwise modified such that other implementations are possible.

A person skilled in the art will be able to practice the present invention after careful review of this description, which is to be taken as a whole. Details have been included to provide a thorough understanding. In other instances, well-known aspects have not been described, in order to not obscure unnecessarily this description.

Some technologies or techniques described in this document may be known. Even then, however, it is not known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious.

The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A method to alert a user or a patient of a wearable cardioverter defibrillator (WCD), the method comprising:
   detecting a condition related to the patient and/or the WCD;
   issuing an alert to notify the user and/or the patient of the condition;
   receiving an input from the user and/or the patient to cause the WCD to enter a silent mode to silence the alert; and
   during the silent mode:
      determining that the condition has been resolved,
      receiving a first input from the user and/or the patient to replay a portion of the alert; and
      replaying the portion of the alert and an indication that the condition has been resolved when the first input is received.

2. The method of claim 1, wherein the portion of the alert comprises at least one of an audible portion of the alert or a visual portion of the alert.

3. The method of claim 1, wherein the condition comprises at least one of a health status of the patient or a status of the WCD.

4. The method of claim 1, further comprising: exiting the silent mode after a predetermined period of time.

5. The method of claim 4, wherein the predetermined period of time is greater than five minutes.

6. The method of claim 1, wherein the alert comprises more than one alert, the method further comprising: replaying the more than one alert in an order of a predetermined priority.

7. The method of claim 1, wherein the alert comprises an audible portion comprising a sound alert and a voice alert.

8. The method of claim 7, wherein in replaying the audible portion further comprises:
   replaying only the voice alert of the audible portion of the alert in response to receiving the first input.

9. The method of claim 1, further comprising:
   playing a status alert message prior to replaying the portion of the alert.

10. A wearable cardiac defibrillator (WCD) system for monitoring health of a patient wearing the WCD system, the system comprising:
    a support structure configured to be worn by the patient; and
    one or more processors configured to cause the WCD system to:
       detect a condition related to the patient and/or the WCD;
    issue an alert to notify the patient and/or a user of the condition;
       receive a selection from the patient and/or the user to cause the WCD to enter a silent mode; and
       during the silent mode:
          determine that the condition has been resolved,
          receive an input from the patient and/or the user to replay a portion of the alert, and
          replay the portion of the alert and an indication that the condition has been resolved in response to the input being received.

11. The WCD system of claim 10, wherein the portion of the alert comprises at least one of an audible portion or a visual portion.

12. The WCD system of claim 10, wherein the condition comprises at least one of a health status of the patient or a status of the WCD.

13. The WCD system of claim 10, wherein the one or more processors are further configured to cause the WCD system to: exit the silent mode after a predetermined period of time.

14. The WCD system of claim 13, wherein the predetermined period of time is greater than five minutes.

15. The WCD system of claim 10, wherein the alert comprises more than one alert, wherein the one or more processors are further configured to cause the WCD system to:
    replay the more than one alert in an order of predetermined priority.

16. A wearable cardioverter defibrillator (WCD) system for monitoring health of a patient using the WCD system, the system comprising:
    a support structure configured to be worn by the patient;
    a plurality of sensors to detect one or more conditions, wherein at least one sensor of the plurality of sensors is configured to be coupled to the support structure;
    one or more displays; and
    one or more processors configured to cause the WCD system to:
       detect a condition related to the patient and/or the WCD system;
       issue an alert to notify the patient and/or a user of the condition;
       receive an input from the patient and/or the user to cause the WCD system to enter a silent mode to silence the alert; and
       during the silent mode:
          determine that the condition has been resolved,
          receive a second input from the patient and/or the user to replay a portion of the alert,
          play a status alert message prior to replaying the portion of the alert, and
          replay the portion of the alert and an indication that the condition has been resolved when the second input is received.

17. The WCD system of claim 16, wherein the portion of the alert comprises at least one of an audible portion or a visual portion.

18. The WCD system of claim 16, wherein the condition comprises at least one of a health status of the patient or a status of the WCD system.

19. The WCD system of claim 16, wherein the one or more processors are further configured to cause the WCD system to:

exit the silent mode after a predetermined period of time.

20. The WCD system of claim 16, wherein the alert comprises more than one alert, wherein the one or more processors are further configured to cause the WCD system to:

replay the more than one alert in an order of predetermined priority.

\* \* \* \* \*